Figure 1:
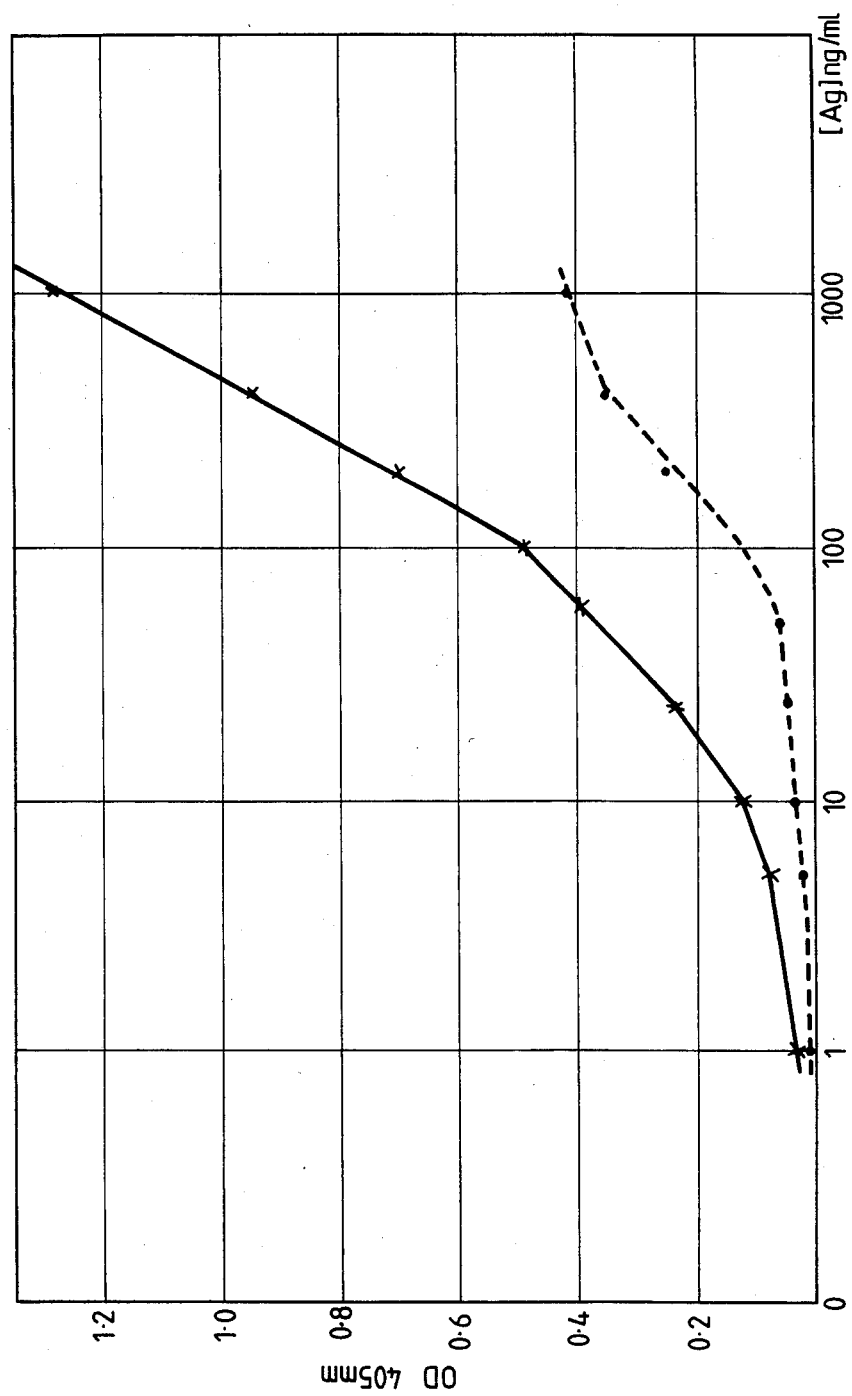
Figure 2:
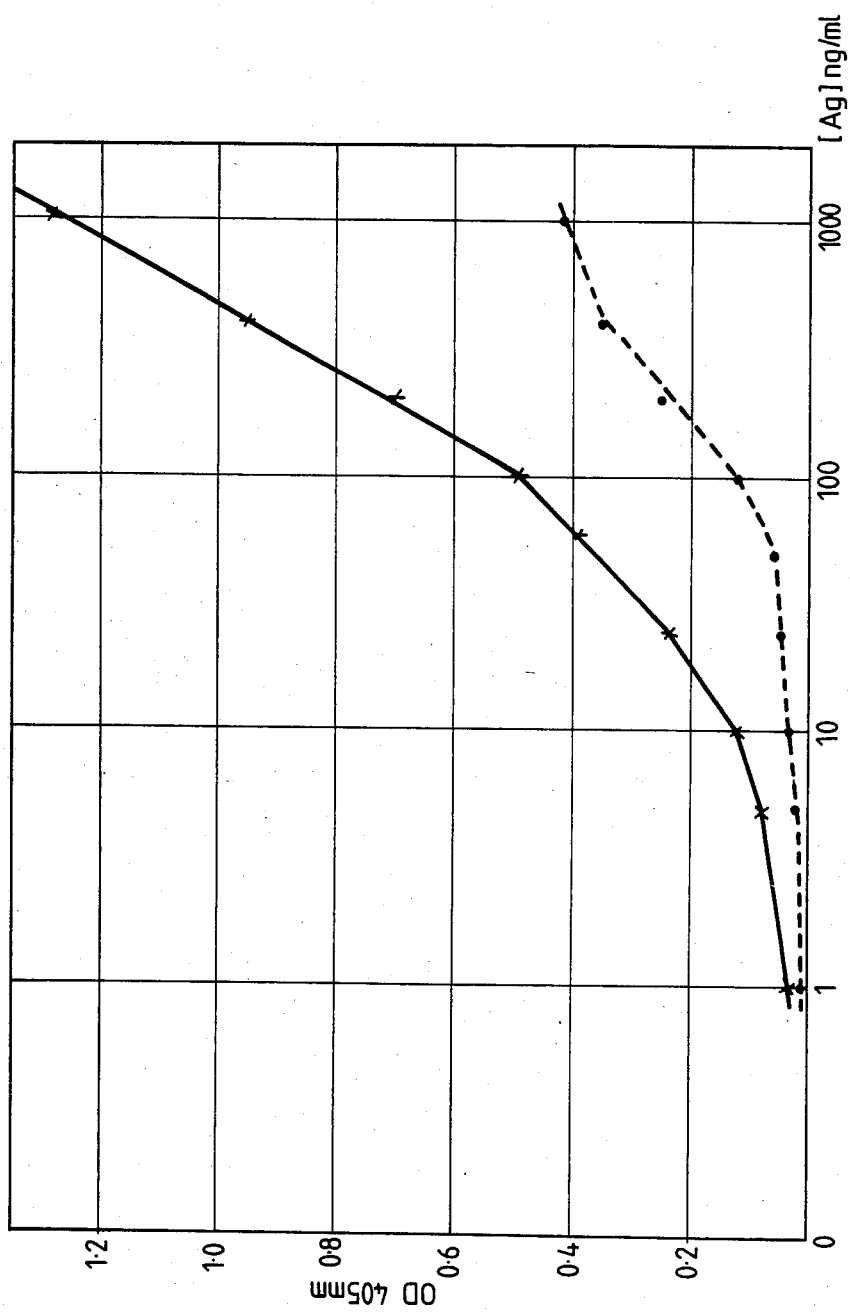

United States Patent [19]

May et al.

[11] Patent Number: 4,659,666

[45] Date of Patent: Apr. 21, 1987

[54] PURE ALKALINE PHOSPHATASE, ITS PREPARATION AND USE

[75] Inventors: Keith May, Bedford; Mohamed M. Gani, Felmersham; Stephanie J. Senior, Bedford, all of Great Britain

[73] Assignee: Internationale Octrooi Maatschappij "Octropa" B.V., Rotterdam, Netherlands

[21] Appl. No.: 665,156

[22] Filed: Oct. 26, 1984

[30] Foreign Application Priority Data

Oct. 28, 1983 [GB] United Kingdom ............... 8328918

[51] Int. Cl.$^4$ ................... C12N 9/96; C12N 9/16; G01N 33/53
[52] U.S. Cl. ............................. 435/188; 435/7; 435/196; 435/810; 435/815
[58] Field of Search ............ 435/7, 21, 188, 196, 435/815, 810; 436/548; 935/108, 110

[56] References Cited

U.S. PATENT DOCUMENTS 4,366,242 12/1982 Neumann et al. .................. 435/21

FOREIGN PATENT DOCUMENTS 0084344 7/1983 European Pat. Off. ............ 435/7
83/03678 10/1983 PCT Int'l Appl. ................. 435/7

OTHER PUBLICATIONS

Chemical Abstracts: 100:83819f 1984 *J. Histochem. Cytochem.* 32(2), 219-29, Cordell, J. et al.
Chemical Abstracts: 99:18486s 1983 *Clin. Chim Acta* 130(2), 199-209, McLaughlin et al.

*Primary Examiner*—Christine M. Nucker
*Assistant Examiner*—Louanne Krawczewicz
*Attorney, Agent, or Firm*—Cushman, Darby & Cushman

[57] ABSTRACT

The enzyme alkaline phosphatase having the following properties:

(i)

molecular weight: approximately 80 000 with 2 subunits of 40 000

(iii)

activator: Mg++
inhibitor: EDTA (iii)

thermal stability: 45° C. or below (iv)

optimum temperature: 35°–45° C.

(v)

pH stability: 6–11

(vi)

pH optimum: 10

(vii)

specific activity: 3000–5000 units/mg (viii)

isoelectric range: between pH 5.0 and 6.0.

An antibody-enzyme conjugate process for purifying alkaline phosphatase and a reagent test kit using the purified alkaline phosphatase are also disclosed.

4 Claims, 1 Drawing Figure

PURE ALKALINE PHOSPHATASE, ITS PREPARATION AND USE

The invention relates to pure alkaline phosphatase and a process for its purification, in particular to such a process involving monoclonal antibody immunoadsorbent techniques.

There is a want for pure alkaline phosphatase in particular for use as an enzyme label in enzyme immunoassays. Relatively pure enzyme material has been commercially available prepared, for example from calf intestine mainly by use of multistep processes involving substrate analogue affinity chromatography techniques. This technique is cumbersome and time consuming. It has now surprisingly been found that by purifying alkaline phosphatase using monoclonal antibody immunoadsorbent techniques a novel, purer, and more active enzyme can be obtained than by means of substrate analogue affinity chromatography or gel fitration technique. This novel, purer alkaline phosphatase, which has a new isoenzyme spectrum profile has the following physical and chemical properties:

(i) molecular weight: approximately 80 000 with 2 subunits of 40 000
(ii) activator: $Mg^{++}$, inhibitor: EDTA
(iii) thermal stability: 45° C. or below
(iv) optimum temperature: 35°–45° C.
(v) pH stability: 6–11
(vi) pH optimum: 10
(vii) specific activity: 3000–5000 units/mg
(viii) isoelectric range: between pH 5.0 and 6.0

Commercially available alkaline phosphatase however, has a specific activity of up to 2500 units/mg and an isoelectric range wider than between pH 4.5 and 6.0. The other properties mentioned above (i–vi) are also typical for the enzyme as already known.

Also its conjugation to antibody is far superior to that of the enzyme purified by substrate analogue affinity chromatography known in the art. This conjugation performance is 3–5 times better and results in higher conversion rates of substrate with the enzyme conjugate in the same time span. Consequently less of the novel purer enzyme can be used for the same purpose than of the known enzyme material as it results in production of more active antibody conjugates. The novel pure alkaline phosphatase has preferably a specific activity between 3500 and 4500 units/mg together with an isoelectric range between pH 5.0 and 5.5. The novel pure alkaline phosphatase is homogeneous from electrophoretic data (between 35 and 45K) and is very low in endo- and exodesoxyribonuclease as to avoid unwanted degradation. It also has a new isoenzyme spectrum profile, which may explain the higher activity.

The novel pure alkaline phosphatase is obtainable from sources such as animal tissue, in particular obtainable from ruminant intestine, more particularly from calf. Methods used so far for concentrating and purifying alkaline phosphase from ruminant intestine material involved a plurality of steps like gelfiltration, ultrafiltration, affinity chromatography etc., and this easily leads to denaturing of the enzyme material and thereby reducing its activity.

In order to obtain alkaline phosphatase of high purity according to the present invention, it is important that the antibody should be one that will specifically bind releasably the alkaline phosphatase but which will not bind other materials that normally occur in the crude starting material. It is not only required that the antibody is specific as to its affinity for alkaline phosphatase but also this affinity must be sufficiently weak in terms of the bond so that it is comparitively easy to effect subsequent release of the alkaline phosphatase from the antibody by means of a minor change in the environment such e.g. a minor change in pH or electrolyte concentration.

Consequently according to the present invention a neutral or alkaline eluant is used in a concentration which does not appreciably denature the enzyme in conjunction with a monoclonal antibody which has an affinity low enough to release the enzyme in the presence of the non-denaturing neutral or alkaline aqueous eluant. Preferably the eluant is selected from the group consisting of neutral or alkaline organic solvent, inorganic salt or polar organic material. More in particular preferred are ethylene glycol (e.g. 50% in water, pH about 10) and $MgCl_2$ (e.g. 1 molar) in phosphate buffered saline.

The invention provides a process for the recovery of pure alkaline phosphatase wherein the source of alkaline phosphatase is contacted with an insoluble carrier material to which is bound a low-affinity antibody specific to the alkaline phosphatase with no cross reactivity with any other common constituent of the source. The antibody binds alkaline phosphatase molecules and following removal of the residue of the source the alkaline phosphatase molecules are released from the antibody. In a preferred embodiment the source of alkaline phosphatase is ruminant intestine material, in particular from calf and the low-affinity antibody is attached to cyanogen bromide Sepharose as the insoluble carrier material (Sepharose is a trade name from Pharmacia Uppsala Sweden for beads of agarose of which the polysaccharide chains cross-linked).

Although cyanogen bromide activated Sepharose is the preferred carrier material it is very well possible to use other carrier material. The carrier can be e.g. nylon, agarose, cellulose, polystyrene, polyacrylamide, carbon fibre, glass, paper, latex or other material that provides immobilization without being degradable under the prevailing conditions. The linking of the antibody to the carrier material is known in the art and a wide variety of techniques are available. The chemical structure of some matrices already contain suitable functional groups and such groups can be used in the coupling reaction or they can be modified if desirable. For other carrier materials which do not inherently contain suitable functional groups, techniques are available for introducing such groups. Functional groups generally require activation, for which a variety of techniques are available.

For example acid hydrolysis of nylon yields abundant free carboxyl (—COOH) and amino (—$NH_2$) groups which can be used for protein linkage. The carboxyl groups can be activated using for example N-hydroxy succinamide esters or N-carbo-diimides. The amino groups can be activated with glutaraldehyde or cyanogen bromide for example. Polysaccharides such as agarose or cellulose naturally contain hydroxyl (—OH) groups, which can be activated using for example, cyanogen bromide or periodate oxidation. Polystyrene and polyacrylamide do not inherently contain any suitable functional groups, but such groups can readily be introduced. For example amino groups can be introduced in polystyrene by nitration and reduction. Following introduction the amino groups can be activated using the procedure for nylon, or if desired can be converted to other functional groups such as hydroxylgroups. Glass can be silylated using commercially available reagents which generally provide amino groups which can be activated as already described.

A monoclonal antibody specific to an enzyme such as alkaline phosphatase can be produced by well-known techniques. A typical procedure will involve injecting purified alkaline phosphatase into a mouse to cause the host to generate antibodies. The mouse is then killed and the spleen removed to yield free spleen cells. These cells fused with Myeloma cells using a standard reagent such as polyethylene glycol, to give hybridoma cells expressing the antibodies. Cell lines expressing antibodies to alkaline phosphatase are selected using enzyme-linked immuno assay (ELISA). Cell lines producing antibodies to the required antigen (alkaline phosphatase) are then selected which allow isolation and release of alkaline phosphatase without loss of enzyme or antibody activity by studying them in elution conditions. What is selected is a specific but low affinity.

Cell lines expressing the selected monoclonal antibodies are cultured further, the expressed antibody fraction purified by chemical means or preferably by an elution procedure analogous to that employed in the affinity selection test and the antibody bound to a solid support system. The immunoadsorbent so obtained can be packed into a column, for example. Such a column can be used repeatedly and the present invention therefore provides a process for the commerical scale production of novel, highly active and pure alkaline phosphatase.

An immunoadsorbent-containing column is incorporated in a conventional processing unit such that at least a substantial proportion of ruminant intestinal preparation throughput of the unit passes through the column. It is normal practice to incorporate filters, made for example from nylon, paper or cotton, in such processing lines and such a filter can be adapted to the purpose of the invention. Preferably, however, the immunoadsorbent unit of the invention is placed downstream from a standard filter. At appropriate intervals, the antibody on the immunoadsorbent column or filter is replaced and the enzyme is recovered from the saturated immunoadsorbent, which is then ready for re-use.

The immunoadsorbent column or filter can be an integral part of a processing line, or it can be utilized as a peripheral processing feature.

An alternative arrangement would be to incorporate the immunoadsorbent column or filter in a recirculation system associated with a bulk holding tank, so that enzyme is recovered from the crude enzyme preparation.

In most arrangements, it will be advantageous to utilize two or more immunoadsorbent columns or filters in parallel. Thus, for example, while one column or filter is being used to extract enzyme, whilst the other is being eluted and made ready for re-use.

To avoid the need for readily-replaceable columns or filter elements, each immunoadsorbent column or filter can be provided with means for elution. Preferably, a means is also provided for flushing each column or filter free of residual enzyme preparation prior to elution and, ideally, free of eluting medium prior to further contact with the preparation. The flushing medium should be a physiologically innocuous liquid, such as dilute aqueous saline solution or phosphate buffered saline (PBS) that will neither harm the immunoadsorbent nor lead to dangerous contamination if any trace amount is carried through.

By means of this process high concentrations of enzyme can not only be recovered quickly and conveniently, but also the comparatively minor amounts of the enzyme alkaline phosphatase present in normal crude enzyme preparation e.g. calf intestine macerate can be recovered economically.

Alkaline phosphatase normally comprises much less than 1% of the total protein of intestinal preparation, for example, so the specificity of the recovery mechanism of the invention leads to removal of the valuable antigenic material leaving the composition of the original natural source material virtually unchanged.

In particular, the enzymatic properties of alkaline phosphatase to which the invention has been applied are essentially unchanged, without denaturation. However, due to greater purity or to a different isoenzyme spectrum it may be more effective.

The present invention also provides an antibody-, hapten- or antigen- conjugate to purified alkaline phosphatase as identified above. Various methods are known in the art to prepare alkaline phosphatase conjugates e.g.

a. One-step glutaraldehyde method
b. Two step glutaraldehyde method
c. Periodate method The enzyme-antibody comprises various antibodies etc. such as anti- beta human chorionic gonadotropin, anti-(hepatitis B)-surface antigen, anti-beta (2) microglobulin, anti-C-reactive protein, anti-ferritin etc. Preferred is the conjugate of beta-human chorionic gonadotropin and pure alkaline phosphatase according to the present invention as defined by the properties mentioned above. As a rule the conjugate comprising alkaline phosphatase according to the present invention shows a conjugation performance which is 3–5 times better than that of the less pure and less active enzyme material known in the art. Consequently less of the novel conjugate material need to be used. The enzyme-conjugate material according to the present invention is useful in enzyme linked immuno assay (ELISA). In particular the present invention provides a reagent test kits for enzyme linked immunoassay comprising an antibody-, hapten- or antigen conjugate to purified alkaline phosphatase as defined hereinbefore. More in particular a pregnancy test kit comprising beta human chorionic gondatropin and pure alkaline phosphatase is provided by the invention. The invention is illustrated by the following examples.

EXAMPLE 1

(a) Preparation of primed splenocytes

Balb/c mice are immunized intraperitioneally with alkaline phosphatase followed by booster immunizations on days 42, 54, and 61. They also received intravenously a booster 3 days before cell fusion. The mice were sacrified and spleen cells prepared aseptically by removing the spleen and teasing the cells into saline. The cell suspension was then centrifuged at 200×g for 5 min, and the pellet resuspended in saline at $10^7$ cells per ml. These steps were carried out at room temperature.

(b) Preparation of Myeloma Cells for Fusion

Balb/c myeloma cells (P3×63. Ag8) derived from the MOPC-21 line and deficient in hypoxanthine guanine phosphoribosyl transferase (HGPRT) were maintained on Delbeco's modified medium (DMEM) containing 10% fetal calf serum and 10% horse serum. The growth of the line was inhibited by selective hypoxanthine aminopterine thymidine medium (HAT). On the day of fusion, the myeloma cell suspensions were centrifuged at $200 \times g$ for 5 min, the pellet resuspended in saline, centrifuged for 5 min at $200 \times g$ and finally suspended in saline at a concentration of $10^7$ cells/ml.

(c) Preparation of Peritoneal Macrophages

On the day before fusion 2–3 adult Balb/c mice were killed, the abdominal skin removed and 4–5 ml saline injected peritoneally, entering directly above the symphysis and letting the tip of the needle rest over the right lobe of the liver. After gentle massage of the abdomen the fluid is withdrawn, yielding $1-3 \times 10^6$ macrophages per mouse. The cells were collected in polypropylene tubes, washed with the DMEM, pooled and counted, then centrifuged for 5 min. at $200 \times g$ and re-suspended in HAT at $5 \times 10^5$ cells/ml. The cells were then distributed at $2-3 \times 10^4$ cells per cup in Linbro tissue culture plates (Flow Laboratories) and trays left in a $CO_2$ incubator ready for use next day.

(d) Fusion

For fusion, $2 \times 10^7$ spleen cells were combined with $5 \times 10^7$ myeloma cells and suspension centrifuged at $200 \times g$ for 5 min. The supernatant was discarded and the pellet loosened. Then to the pellet 1.0 ml of 50% solution (w/v) of polyethylene glycol (PEG) 3000 or 0.2 ml of 35% solution (w/v) of PEG 1500 was added. The cells were incubated for 1 min. under constant agitation at room temperature followed by immersion for 2 min. without agitation in a 37° C. water bath. The fusion was stopped by slowly adding 20 ml saline over the next 5 min. The cells were centrifuged for 5 min. at $200 \times g$. The supernatant was discarded and the pellet gently resuspended in HAT. The cells were then distributed at a concentration of $7 \times 10^4$ (spleen) cells per cup in Linbro plates treated a day before with $2-3 \times 10^7$ macrophages per cup. The plates then incubated at 37° C. in 16% $CO_2$ incubator.

(e) Maintenance

Cultures were inspected on days 4, 7, 10 and then every other day, up to the end of the third week. On each of these days, 1 ml of medium was removed by suction and replaced by fresh HAT medium up to day 21 and then by normal growth medium thereafter. The supernatant from wells containing more than $10^4$ hybrid cells was tested for antibodies to alkaline phosphatase using an enzyme linked immunoassay. The positive clones were then transferred to a 25 cm² flask containing 2 ml fresh medium.

As soon as the hybrids had grown to almost confluence in the 25 ml flasks, the cells were frozen in 10% DMSO and samples injected into pristane-treated mice. Ascitic fluid was collected from these mice after 15 days. The fluid contained approximately 3 mg per ml of the specific monoclonal antibody. Alternatively antibody was produced by selected growth hybridomas in Vitro.

(f) Suitability of antibodies for enzyme isolation

Antibodies were considered suitable if they allowed isolation without damage to the enzyme activity. The suitability of the antibodies for the purpose of the invention was assessed by coupling purified monoclonal antibodies to cyanogen bromide sepharose. Crude or purified alkaline phosphatase was then passed down the column and the unbound material washed free with phosphate buffer. The specifically bound enzyme was then released by treatment of the column with a mild releasing agent in this case ethylene glycol pH 11. A mild releasing agent (ethylene glycol/water 50:50 pH 11.5) was defined as a reagent which allows release of the enzyme from the immunoadsorbent without damaging the enzyme (i.e. without reducing the enzyme alkaline phosphatase from bovine int. activity).

EXAMPLE 2

Example 1 was repeated with some changes indicated below:
(a) remained identical
(b–d) replaced by the procedure outlined below
(e–f) remained identical
Fusion:
For fusion, $2 \times 10^7$ spleen cells were combined with NS1 or SP20 $4.5 \times 10^7$ cells and the suspension centrifuged at $200 \times g$ for 5 minutes. The supernatant was discarded and the pellet loosened. Then to the pellet 1.0 ml of 50% solution (w/v) of polyethylene glycol (PEG). 3000 was added. The cells were gently centrifuged for 3 minutes at $200 \times g$. After a total contact time of 8 minutes, the cells were re-suspended in 5 ml PBS-glucose and centrifuged ($200 \times g$) for a further 5 minutes. The supernatant was discarded and the pellet gently re-suspended in 20 ml PBS-glucose for a final wash. The cells were centrifoged for 5 minutes at $200 \times g$. The supernatant was discarded and the pellet gently resuspended in HAT. The cells were then distributed at $7 \times 10^4$ (spleen) concentration per cup in the pre-treated Limbroplate. The plates were incubated at 37° C. in a 6% $CO_2$ incubator.

EXAMPLE 3

The enzyme purified by one of the selected antibodies was characterized as having a restricted iso-enzyme profile between pH 5.0 and 6.0, usually between 5.0 and 5.5 and a specific activity of 3500 sometimes 4000 U/mg compared to commercially available material purified by conventional techniques which typically had an activity of 2500 U/mg and an iso-enzyme profile between pH 4.5 and 6.0.

EXAMPLE 4

The enzyme described in example 3 was conjugated to rabbit antibodies to human liver ferritin. 0.3 mg of Ab (in 100 μl) was added to 1.0 mg of enzyme (in 100 μl) and 5 μl of 25% glutaraldehyde added. This was incubated for 3–4 hours at room temperature. After this time the mixture was added to a solution containing 0.5 mg ovalbumin, 0.002% thermersal, 0.002% sodium azide in 0.05M tris HCl pH 8.0.

Its performance was then compared in enzyme linked immunoassay (ELISA) to that of a conjugate prepared with a commercially available alkaline phosphatase of high specific activity (above 2500 U/mg).

Performance in ELISA

Solid surfaces e.g. polystyrene wells were coated with antibodies to human liver ferritin. A 5–50 μg/ml solution of antibody added to wells in pH 9.5 carbonate buffer and incubated overnight at 37° C. The wells were then washed out $6 \times$ with phosphate buffered saline containing 0.1% tween (PBST). A range of human liver ferritin solutions 0–1000 ng/ml were added to the wells and incubated for 2 hours at 37° C. The wells were then washed 6× with PBST. 200 ml of the conjugate was then added at 1/200 dilution to each of the wells and incubated for 2 hours at 37° C. The wells were then washed with PBST. 200 μl of 5 μg/ml solution of paranitrophenylphosphate was then added to each well and incubated for 30 minutes at 37° C. and the plate read on a Dynatech (MR 580-automatic) plate reader. The optical density was then plotted against ferritin concentration (FIG. 1). The performance of the conjugate prepared with alkaline phosphatase described in example 2 was 3–4× better than that of the conjugate prepared with commercially available enzyme.

EXAMPLE 5

The process of Example 4 first paragraph was repeated, however, substituting the antibodies to human liver ferritin for sheep antibodies to beta human chorionic gonadotropin. This resulted in the preparation of a highly active conjugate with pure alkaline phosphatase of Example 3 which proved useful in enzyme linked immunoassay test kits.

EXAMPLE 6

The enzyme described in example 3 was conjugated to sheep antibodies to beta human chorionic gonadotropin (BHCG) 0.3 mg of Ab (in 100 μl) was added to 1.0 mg of enzyme (in 100 μl) and 5 μl of 25% glutaraldehyde added. This was incubated for 3–4 hours at room temperature. After this time the mixture was added to a solution containing 0.5 mg ovalbumin, 0.002% thermersal, 0.002% sodium azide in 0.05M tris HCl pH 8.0.

Performance in ELISA

Polystyrene wells were coated with the antibodies to BHCG. A 5–50 μg/ml solution of antibody added to wells in carbonate buffer and incubated overnight at 37° C. The wells were then washed out 6× with phosphate buffered saline containing 0.1% tween (PBST). A range of BHCG solutions 0–1000 ng/ml were added to the wells and incubated for 2 hours at 37° C. The wells were then washed 6× with PBST. 200 ml of the conjugate was then added at 1/200 dilution to each of the wells and incubated for 2 hours at 37° C. The wells were then washed with PBST. 200 μl of 5 μg/ml solution of paranitrophenylphosphate was then added to each well and incubated for 30 minutes at 37° C. and the plate read on a Dynatech (MR 580-automatic) plate reader. This showed that an enzyme-conjugate useful in ELISA had been obtained.

We claim:

1. The enzyme alkaline phosphatase which has the following physical and chemical properties:

(i)

molecular weight: approximately 80 000 with 2 subunits of 40 000

(ii)

activator: $Mg^{++}$ inhibitor: EDTA (iii)

thermal stability: 45° C. or below (iv)

optimum temperature: 35°–45° C.

(v)

pH stability: 6–11

(vi)

pH optimum: 10

(vii)

specific activity: 3000–5000 units/mg (viii)

isoelectric range: between pH 5.0 and 6.0.

2. Alkaline phosphatase according to claim 1 characterized in that the specific activity is from 3500–4500 units/mg and the isoelectric range between pH 5.0 and 5.5.

3. An antibody-enzyme conjugate wherein the enzyme is the alkaline phosphatase of claim 1.

4. The antibody-enzyme conjugate of claim 3 wherein the antibody is anti-beta human chorionic gonadotropin.

* * * * *